(12) United States Patent
Eisele

(10) Patent No.: US 7,699,840 B2
(45) Date of Patent: Apr. 20, 2010

(54) NEUTRAL ELECTRODE FOR HF SURGERY

(75) Inventor: Florian Eisele, Tubingen (DE)

(73) Assignee: ERBE Elektromedizin GmbH, Tübingen (DE)

( * ) Notice: Subject to any disclaimer, the term of this patent is extended or adjusted under 35 U.S.C. 154(b) by 292 days.

(21) Appl. No.: 10/598,566

(22) PCT Filed: Feb. 18, 2005

(86) PCT No.: PCT/EP2005/001712

§ 371 (c)(1),
(2), (4) Date: Sep. 5, 2006

(87) PCT Pub. No.: WO2005/087124

PCT Pub. Date: Sep. 22, 2005

(65) Prior Publication Data

US 2007/0167695 A1    Jul. 19, 2007

(30) Foreign Application Priority Data

Mar. 5, 2004  (DE) ........................ 10 2004 010 940

(51) Int. Cl.
*A61B 18/16* (2006.01)
(52) U.S. Cl. ...................................... 606/32
(58) Field of Classification Search ............. 606/32
See application file for complete search history.

(56) References Cited

U.S. PATENT DOCUMENTS 3,848,600 A * 11/1974 Patrick et al. .......... 606/32
4,387,714 A * 6/1983 Geddes et al. .......... 606/32
5,178,879 A   1/1993 Adekunle et al.
5,505,715 A * 4/1996 Shah et al. ............. 604/290
6,544,258 B2 * 4/2003 Fleenor et al. .......... 606/32
2001/0029370 A1  10/2001 Hodva et al.
2002/0072744 A1   6/2002 Harrington et al.
2002/0193789 A1  12/2002 Underwood et al.

FOREIGN PATENT DOCUMENTS

| | | |
|---|---|---|
| CN | 1353592 A | 6/2002 |
| CN | 1446574 A | 10/2003 |
| DE | 1 170 085 A1 | 5/1964 |
| DE | 28 30 412 A1 | 1/1980 |
| DE | 3323833 A1 | 1/1985 |
| DE | 198 54 290 A1 | 5/2000 |
| EP | 1 036 540 A1 | 9/2000 |
| EP | 1 048 294 A2 | 11/2000 |
| EP | 0 625 034 B1 | 6/2002 |
| EP | 1 281 393 A2 | 2/2003 |
| EP | 1 282 393 B1 | 11/2005 |

* cited by examiner

*Primary Examiner*—Lee S Cohen
(74) *Attorney, Agent, or Firm*—Dickstein Shapiro LLP

(57) ABSTRACT

The invention relates to a neutral electrode for HF surgery and to an electrically conductive gel. The neutral electrode comprises at least one electrically conductive section that can be brought into contact with a section of a patient's body. In order to enable the contact resistance to be reduced in a simple and economical manner, in particular in cases of problematic skin and/or tissue conditions, the neutral electrode comprises circulation-promoting means that enhance blood flow through the section of the body that is in contact with this electrode section. The invention also relates to a conductive gel for application of a neutral electrode to a section of a patient's body that contains capsaicin or similar means for promoting circulation.

3 Claims, 3 Drawing Sheets

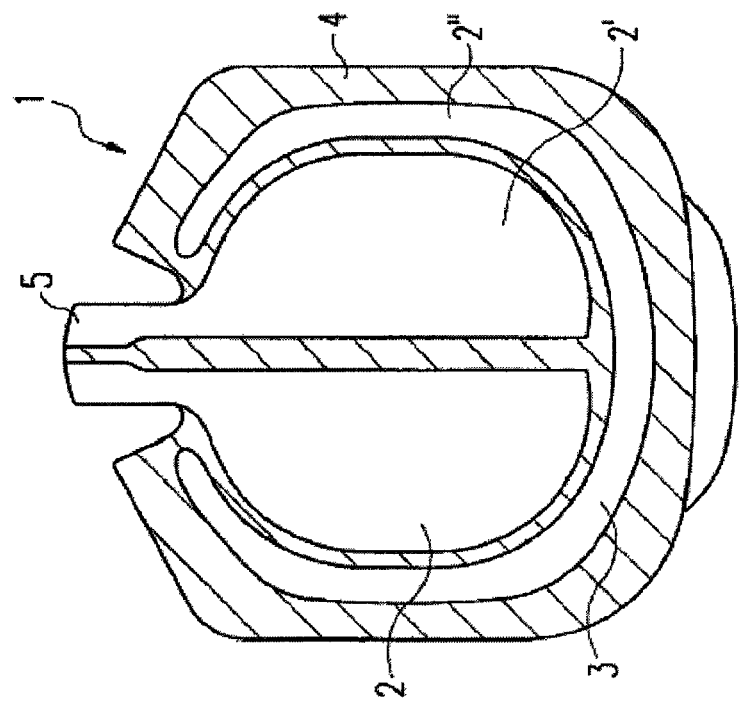
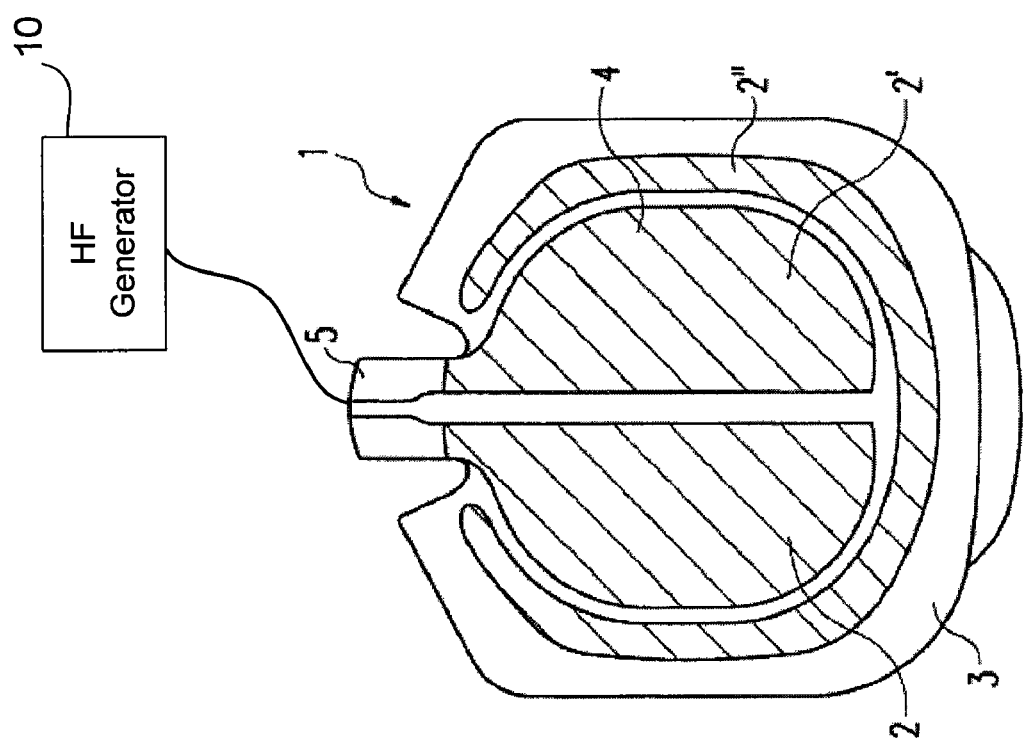

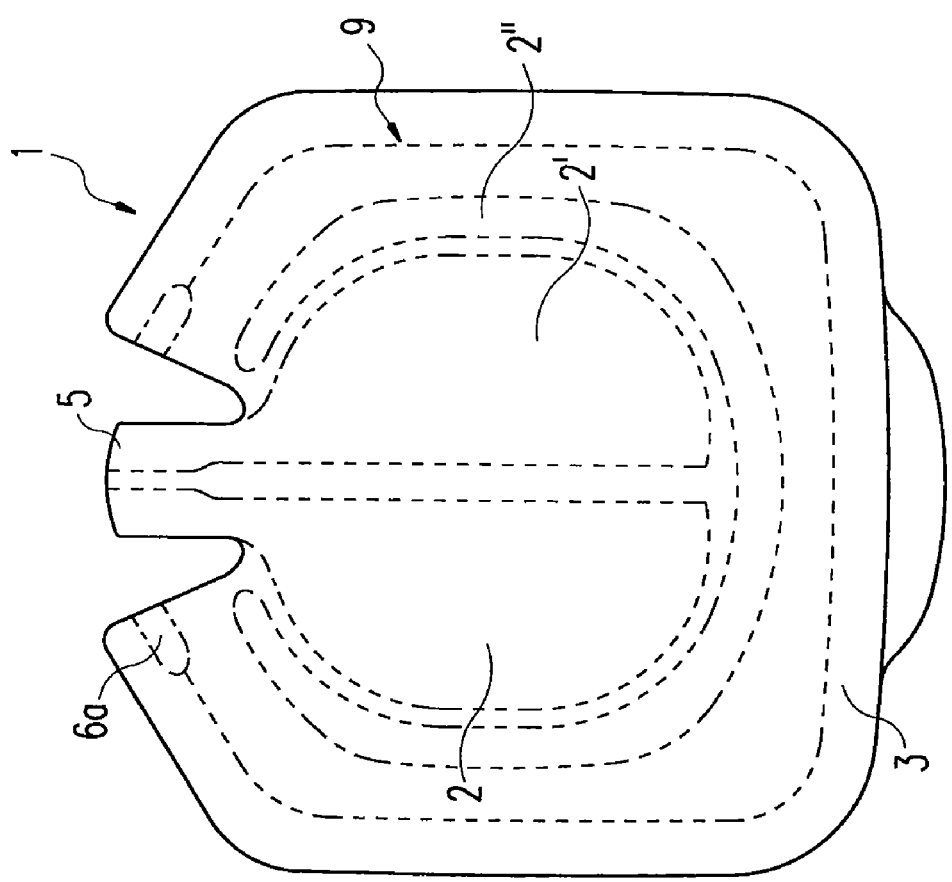

NEUTRAL ELECTRODE FOR HF SURGERY

CROSS-REFERENCE TO RELATED APPLICATIONS

This application is a section 371 of International Application No. PCT/EP2005/001712, filed on Feb. 18, 2005, which was published in the German language on Sep. 22, 2005, under International Publication No. WO 2005/087124 A1 and the disclosure of which is incorporated herein by reference.

BACKGROUND OF THE INVENTION

The present invention relates to a neutral electrode for HF surgery and to a conductive gel for use with such a neutral electrode.

When employing neutral electrodes care should always be taken to keep the contact resistance between the skin and the electrode apposed thereto from becoming too high, so as to prevent excessive warming of the human tissue by a flowing HF treatment current. High contact resistances occur primarily in patients with extremely dry skin, in adipose patients because of the high fat content of the tissue, or in some cases of very hairy skin, when the dense hairs prevent complete contact between electrode and skin. The hairs can easily be removed by shaving. To deal with the problems of dry skin or adipose tissue, however, is distinctly more difficult. In order to prevent severe warming or even burning of the human tissue, therefore, the customary neutral electrodes have large surface areas, which counteract high current densities. Often several electrodes are employed in order to enlarge the effective area and thus reduce the current density.

The reduction of contact resistance, in particular when there are problematic skin and/or tissue conditions, can often be accomplished only by the use of multiple electrodes or by making an electrode larger. However, this increases the costs and furthermore makes it more difficult to manipulate the electrodes.

BRIEF SUMMARY OF THE INVENTION

It is an object of the invention to provide a neutral electrode for HF surgery for-particular use with patients with problematic skin and/or tissue conditions, by a reduction of the contact resistance in a simple and economical manner, and to provide an electrically conductive gel for use in the application of the neutral electrode.

According to the invention a neutral electrode for HF surgery comprises at least one electrically conductive section that can be brought into contact with a portion of a patient's body, and also comprises means for promoting blood circulation, which enhance blood flow at least within the portion of the body that makes contact with this electrode section.

Also according to the invention there is provided a conductive gel for use in the application of a neutral electrode to a body section of a patient, wherein the conductive gel comprises capsaicin or a similar substance that promotes blood circulation.

A basis of the invention resides in the fact that the insulating action of tissue surrounding blood vessels is reduced by blood flow through the finest capillaries. This enhanced flow can be achieved by using an appropriately configured neutral electrode and/or a gel that can be put onto the neutral electrode just before it is used. The conductive gel that contains the circulation-promoting agent and can, for example, be applied from a tube is available for all kinds of electrodes.

The at least one electrically conductive section of the neutral electrode in a preferred embodiment is coated with a conductive gel. As a result, the contact between electrode and skin is ensured.

Preferably the circulation-promoting means comprise a substance that contains a circulation-promoting agent. Because the tissue surrounding the blood vessels in principle has insulating properties, these can be counteracted when there is a high degree of blood flow through the tissue. With the help of the circulation-promoting substance, therefore, the contact resistance is reduced. This is advantageous in particular in the case of patients with dry skin and/or with adipose tissue below the skin.

In another preferred embodiment the at least one electrically conductive section of the neutral electrode is coated with the substance containing the circulation-promoting agent. As a result, the region of the body section that receives enhanced blood flow is precisely the region crucial for the contact resistance, namely the tissue that is covered by the electrically conductive section.

Preferably the conductive gel contains the substance that includes the circulation-promoting agent. In this embodiment the increase of blood circulation can be obtained in a particularly simple and economical manner. The neutral electrode to which the conductive gel containing the circulation-promoting substance has already been applied is used in the same way as conventional neutral electrodes. The improved current conductivity between tissue and electrode can thus be achieved without any great effort, with no need for any special or even additional measures to be taken by the operating-theatre personnel.

In one possible implementation of the neutral electrode, the substance comprising the circulation-promoting agent is contained in the carrier material that encloses the at least one electrically conductive section. Often the electrically conductive sections of the neutral electrode are attached to the corresponding body section by adhesion, in which case the section is surrounded, e.g., by self-adhesive material. The circulation-promoting agent contained in the carrier material then enters the tissue covered by the neutral electrode immediately after the neutral electrode has been applied to the relevant section of the patient's body. The size of the carrier material can be adapted to the amount of agent required; for example, it may have a larger area than is the case for conventional electrodes. Incorporation of the agent into the carrier material is particularly useful when neutral electrodes are not delivered with the conductive gel, but must instead be provided with the gel by the operating-theatre personnel immediately before use. Furthermore, the substance containing the agent cannot be accidentally removed, as can easily happen to gel layers when they are contacted by chance. Hence it is ensured that agent is always present in its entirety.

In another advantageous embodiment of the neutral electrode in accordance with the invention the circulation-promoting means comprise elements that supply a stimulating current, for instance electrically conductive sections. In this case circulation through the part of the patient's body covered by the neutral electrode is enhanced by this electrical current. This is particularly advantageous for patients who exhibit allergic reactions to circulation-promoting chemicals. In the case of re-usable neutral electrodes, furthermore, the employment of a stimulus current is a simple and economical means of enhancing blood flow and thus keeping the contact resistance between skin and electrode low, or even reducing it.

It is further provided as one of the preferred embodiments that the elements conducting the stimulus current are disposed so that the stimulus current flows between at least two sections within the neutral electrode. It is advantageous that the conventional neutral electrode can thus be used to transmit the stimulus current. With this embodiment no additional components are required at the neutral electrode. As a result, the circulation is enhanced in the most simple and economical manner.

In another preferred embodiment, the solution in accordance with the invention provides that the elements supplying the stimulus current comprise separate electrical connecting devices by way of which a current source is connected. The advantage here is that the stimulus current can be supplied independently of the high-frequency generator, for instance by means of a supplementary current source.

Alternatively or in addition it is possible for the stimulus current to be supplied by way of two further electrodes that have been embedded in the carrier material and additional conductor leads that have likewise been embedded in the carrier material. In this case, again, the carrier material could, e.g., have a larger area than that found in conventional neutral electrodes. Then the supply of stimulus current is advantageously entirely independent of whether the electrodes are in use.

Another preferred embodiment provides that the circulation-promoting means comprise heatable elements. For this purpose the carrier material comprises, on a side that faces away from the skin, fixation means such as snap fasteners or Velcro strips to retain a heat-storing element, e.g. in the form a gel cushion. The blood flow can thus advantageously be promoted efficiently and in an extremely skin-friendly manner.

In another preferred embodiment the circulation-promoting means comprise elements that can be heated by a direct supply of energy, for instance resistance or heating wires that have been incorporated into the carrier material and are provided with appropriate connector devices. For this purpose the carrier material is preferably designed with a larger area than that of a standard electrode. Connection to the heating device is easily performed, so that promotion of blood flow can be simply and rapidly accomplished.

The invention will now be described by way of example with reference to the attached drawings.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 is an end elevation of a first embodiment of neutral electrode for HF surgery showing the side that faces the skin;

FIG. 2 is an end elevation of a second embodiment of neutral electrode for HF surgery showing the side that faces the skin;

FIG. 5 is an end elevation of a fifth embodiment of neutral electrode for HF surgery showing the side that faces away from the skin.

DETAILED DESCRIPTION OF THE INVENTION

Figure 4:
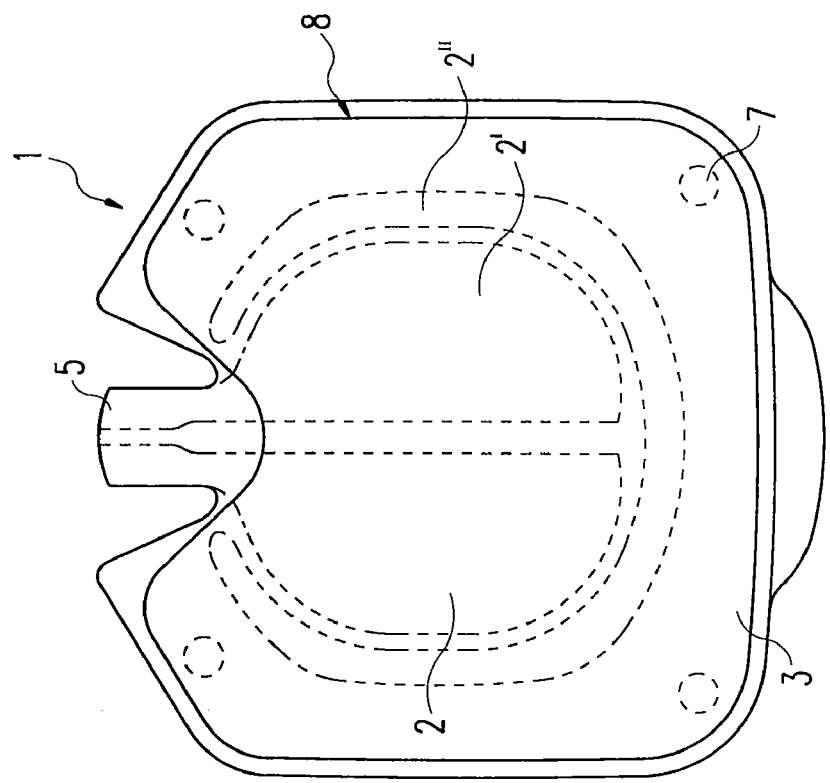
FIG. 4 is an end elevation of a fourth embodiment of neutral electrode for HF surgery showing the side that faces away from the skin.

In the following description, the same reference numerals are used for identical parts or parts with identical actions.

These illustrations of exemplary embodiments show neutral electrodes 1 with an equipotential ring that forms a region with electrically conductive sections 2″. It should, however, be pointed out that the present invention is applicable to every kind of electrode, in particular conventional electrodes without an equipotential ring.

FIG. 1 shows a first embodiment of the invention, with sections 2, 2′ and 2″ and corresponding connector devices 5. Connector devices 5 are connected to HF-generator 10. The surface shown here is the one facing the skin. The sections 2, 2′ and 2″ are here placed on a carrier material 3, and a substance 4 containing a circulation-promoting agent has been applied to the electrically conductive sections 2, 2′ and 2″ of the neutral electrode 1.

Neutral electrodes are often manufactured in such a way that a conductive gel that is needed for the contact between electrode and human tissue and has already been applied to the electrically conductive sections. It is then advantageous for this gel additionally to incorporate the substance 4 containing the circulation-promoting agent, so that the neutral electrode 1 can be put into position with no special effort, in particular without any additional step in the work of the operating personnel. The application of the gel containing the circulation-promoting substance 4 to the electrically conductive sections 2, 2′ and 2″ guarantees that when the electrode 1 is in use, blood flow will be optimal precisely in those parts of a patient's body through which the current is flowing back to the neutral electrode 1. On one hand, the gel causes the electrode 1 to be uniformly apposed to the tissue, while on the other hand it conducts the current and thus produces a suitable contact resistance during the operation. The circulation-promoting substance 4 reinforces the effect of the gel and helps to lower the contact resistance.

Alternatively it is possible to apply to the electrically conductive sections 2, 2′ and 2″ only the substance 4, which contains the circulation-promoting agent. This possibility is applicable, for example, when no conductive gel is to be used during employment of the electrode 1.

FIG. 2 shows a second embodiment of the neutral electrode 1, in which the substance 4 containing the circulation-promoting agent is applied to the carrier material 3 of the neutral electrode 1, i.e. the material comprising the electrically conductive sections 2, 2′ and 2″. Again, a side that faces towards the skin is shown here.

As soon as the carrier material 3 comes into contact with the skin, the agent diffuses into the tissue and exerts its warming and/or circulation-promoting effect. To optimize blood flow through the skin underlying the neutral electrode 1, one possibility is to provide both the electrically conductive sections 2, 2′ and 2″ and the carrier material 3 with the relevant substance 4. Especially in the case of adipose patients, an adequate blood circulation can thus be obtained.

Figure 3:
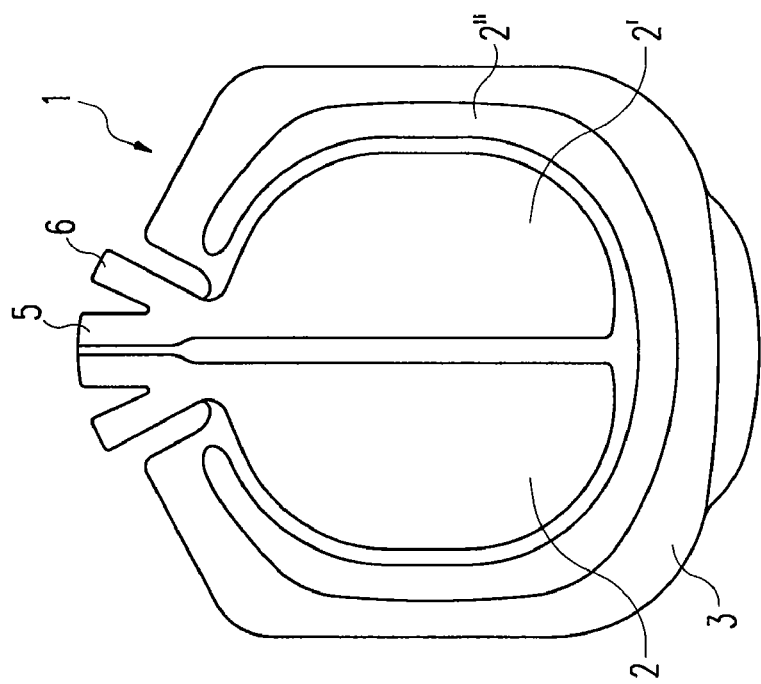
FIG. 3 is an end elevation of a third embodiment of neutral electrode for HF surgery showing the side that faces the skin.

A third embodiment of the invention is shown in FIG. 3. Again, a side facing towards the skin is represented. This embodiment allows a stimulus current to be introduced into the human tissue covered by the neutral electrode 1, for which purpose the sections 2, 2′ are designed as elements to supply the stimulus current. This embodiment exhibits both the conventional connector devices 5 of the sections 2, 2′ disposed on the carrier material 3 and also additional connector devices 6.

The stimulus current can thus be supplied by way of the electrically conductive sections 2, 2′ and the connector devices 5 of the sections 2, 2′, which are already present, or also by way of separate connector devices 6. The connector devices 6 enable current to be supplied from a current source independent of a HF generator. It is also possible to provide supplementary conductive sections (not shown) that serve exclusively to transmit the stimulus current. Then additional, supplementary connector devices should be provided for the supplementary sections. The promotion of blood flow by means of a stimulus current is preferable, for example, when patients exhibit allergic reactions to particular circulation-promoting chemicals.

FIG. 4 shows a fourth embodiment of the neutral electrode 1, as seen from the side that faces away from the skin. The carrier material 3 that holds the sections 2, 2', 2" here comprises fixing devices 7 for the fixation of heatable and heat-storing elements 8, for instance counterparts of snap or Velcro fasteners. The carrier material 3 is therefore enlarged in this embodiment.

The element 8, e.g. a gel cushion, can be attached to the electrode 1 while in a warm state prior to the operation, and then gradually release the stored heat. While this occurs, the neutral electrode 1 can be covered by the elements 8 either completely or only partially. Partial covering is advisable when the view should not be obstructed, because visual monitoring of the contact between electrode and body section is necessary.

FIG. 5 shows a fifth embodiment of the invention, again representing the side that faces away from the skin. The neutral electrode here comprises an element 9 that can be heated by a direct supply of energy, with connector devices 6a. Warming of the skin tissue in this case is brought about by resistor wires or heating wires 9 that are incorporated into the carrier material 3 and enclose the sections 2, 2' and 2".

Depending on the intended application, a combination of various circulation-promoting means is to be recommended in order to minimize the contact resistance between tissue and electrode, in particular also in adipose patients.

List of Reference Numerals
1 Neutral electrode
2, 2', 2" Electrically conductive section
3 Carrier material
4 Substance containing a circulation-promoting agent
5 Connector devices
6 Connector devices
6a Connector devices
7 Fixing device
8 Warmable elements
9 Heatable elements It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An HF-generator with a neutral electrode for high frequency (HF) surgery, the electrode comprising at least one electrically conductive section for contacting a patient's body, wherein the at least one electrically conductive section is coated with a gel containing a circulation promoting agent as a circulation promoting means adapted to enhance blood flow at least through said body portion in contact with said at least one electrically conductive section and to reduce a contact resistance between said conductive section and said body portion.

2. The HF-generator according to claim 1, wherein the circulation promoting agent is capsaicin.

3. An HF-generator with a neutral electrode for use in high frequency (HF) surgery, the electrode comprising:

at least one electrically conductive section for contacting a patient's body, wherein said section is coated with a conductive gel to improve the contact between said section and said portion of the patient's body and wherein said gel incorporate a substance that contains a circulation promoting agent as a circulation promoting means adapted to enhance blood flow at least though said body portion in contact with said at least one electrically conductive section.

* * * * *